United States Patent
Mann et al.

(10) Patent No.: US 9,581,602 B2
(45) Date of Patent: Feb. 28, 2017

(54) METHOD OF SELECTING A MONOCLONAL CELL COLONY

(71) Applicant: Molecular Devices, LLC, Sunnyvale, CA (US)

(72) Inventors: Christopher John Mann, New Milton (GB); Julian Francis Burke, Winchester (GB); Alasdair Macmillan Robertson, Bournemouth (GB)

(73) Assignee: Molecular Devices, LLC, Sunnyvale, CA (US)

( * ) Notice: Subject to any disclaimer, the term of this patent is extended or adjusted under 35 U.S.C. 154(b) by 247 days.

(21) Appl. No.: 14/428,382

(22) PCT Filed: Sep. 13, 2013

(86) PCT No.: PCT/US2013/059758
§ 371 (c)(1),
(2) Date: Mar. 16, 2015

(87) PCT Pub. No.: WO2014/043532
PCT Pub. Date: Mar. 20, 2014

(65) Prior Publication Data
US 2015/0268249 A1 Sep. 24, 2015

(30) Foreign Application Priority Data
Sep. 14, 2012 (EP) .................................... 12184418

(51) Int. Cl.
*G01N 33/68* (2006.01)
*C12M 1/34* (2006.01)
*C12M 1/32* (2006.01)

(52) U.S. Cl.
CPC ......... *G01N 33/6854* (2013.01); *C12M 23/12* (2013.01); *C12M 41/00* (2013.01)

(58) Field of Classification Search
None
See application file for complete search history.

(56) References Cited

U.S. PATENT DOCUMENTS

| 5,106,584 A | 4/1992 | Funakubo et al. |
| 7,598,093 B2 | 10/2009 | Lehmann et al. |
| 2003/0143642 A1 | 7/2003 | Jesperson et al. |

FOREIGN PATENT DOCUMENTS

| EP | 2166511 A1 | 3/2010 |
| EP | 2437057 A1 | 4/2012 |
| JP | 2005055411 | 3/2005 |
| WO | 03019137 | 3/2003 |
| WO | 2005-045396 A2 | 5/2005 |

OTHER PUBLICATIONS

Burke et al. (Bioprocess International 2006 p. 48-51 ).*
International Search Report from International Patent Application No. PCT/US2013/059758, dated Nov. 7, 2013.

* cited by examiner

*Primary Examiner* — Jacob Cheu
(74) *Attorney, Agent, or Firm* — Bella Fishman

(57) ABSTRACT

A method of selecting a monoclonal cell colony that secretes a product of interest providing a plurality of cell culture spaces; each cell culture space has a respective assessment surface with a first binding agent immobilized on the assessment surface. The cells are incubated in a growth medium in the cell culture spaces for replication of the cells. At least some of the cells secrete a product of interest. A second binding agent is provided in the cell culture spaces. Initially, the second binding agent is not immobilized. Each of the first and second binding agents binds to the product of interest so that secretion of the product of interest by cells in any one of the cell culture spaces leads to a complex with the first binding agent, the product of interest and the second binding agent forming at the corresponding assessment surface of the cell culture space.

12 Claims, 4 Drawing Sheets

METHOD OF SELECTING A MONOCLONAL CELL COLONY

This application claims the benefit of European Patent Application Serial No. 12184418.7, filed Sep. 14, 2012, the content of which is incorporated by reference herein in its entirety.

The invention relates to a method of selecting a monoclonal cell colony that secretes a product of interest.

In a known method, cells from a heterogeneous mixture of cells are plated using limiting dilution in the wells of a multi-well plate. The formation of monoclonal cell colonies can be assessed by white light imaging of the cells in the wells. However, an assessment of secretion of a product of interest requires a respective aliquot to be taken from each well and analysed for the product of interest. The taking and analysis of the aliquots complicates the method undesirably.

According to a first aspect of the invention, there is provided a method of selecting a monoclonal cell colony that secretes a product of interest, comprising: providing a plurality of cell culture spaces, each cell culture space having a respective assessment surface; providing each said assessment surface with a first binding agent that is immobilised on the assessment surface; plating a suspension of cells in the plurality of cell culture spaces so that at least some of the cell culture spaces are plated with a single viable cell; incubating the cells in a growth medium in the cell culture spaces to cause replication of the cells, wherein at least some of the cells secrete a product of interest; providing a second binding agent in the cell culture spaces, the second binding agent not being immobilised; wherein each of the first and second binding agents binds to the product of interest so that secretion of the product of interest by cells in any one of the cell culture spaces leads to a complex comprising the first binding agent, the product of interest and the second binding agent forming at the corresponding assessment surface of the said one cell culture space; assessing each of at least some of the cell culture spaces for presence of the second binding agent at the assessment surface of the cell culture space; determining for each of at least some of the cell culture spaces whether the cell culture space contains a single cell colony that is derived from a single cell; and selecting a cell culture space using said assessment and said determination, the selected cell culture space containing a single monoclonal cell colony which secretes the product of interest.

The term "monoclonal", as used herein, refers to a plurality of cultured cells that are derived from a single ancestral cell by cell replication. Preferably, the cells will be eukaryotic cells although the method is applicable to other cell types. As used herein "selecting" means choosing and does not require removal of a monoclonal cell colony from the cell culture space. The term "secrete" as used herein covers the production by a cell and the release into the extracellular space of a product of interest by any mechanism. Generally the mechanism will be one which does not kill the cell and which leaves a viable cell with continuing capability to secrete the product of interest. For example, where the cells are eukaryotic, the product of interest may be secreted by a classical secretion pathway involving the rough endoplasmic reticulum, Golgi apparatus and secretory vesicles. Alternatively, the product of interest may be secreted by any known or unknown non-classical secretion mechanism.

The product of interest is preferably a polypeptide or a protein. In this case, the polypeptide or protein may be glycosylated and/or may have undergone any other post-translational modification. More preferably, the product of interest is an antibody or a fragment of an antibody.

The cell culture spaces are independent of one another in the sense that growth medium in one cell culture space is not in fluid communication with growth medium in any other cell culture space. Preferably, the cell culture spaces are, respectively, wells of a multi-well culture plate. For example, the cell culture spaces may be wells of a 96 well plate or of a 384 well plate. Alternatively, the cell culture spaces could be provided by respective separate culture vessels.

For each cell culture space, the associated assessment surface contacts the growth medium that is used in that cell culture space during incubation of the cells. Each assessment surface is preferably an integral surface of the cell culture vessel that provides the associated cell culture space. Alternatively, the assessment surface may be a surface of an insert that is placed in the culture vessel. Where the cell culture spaces are wells of a multi-well plate, each assessment surface is preferably a bottom, upwardly-facing surface of the associated well. In this case, the bottom surface may be a planar, upwardly facing, horizontal surface. In an especially preferred embodiment, each cell culture space is a well of a multi-well plate and each assessment surface is a bottom, upwardly-facing, concave surface. When a cell is plated into a well with a concave bottom surface, the concave shape of the bottom surface tends to direct the cell towards the middle of the bottom surface, which is the lowest point of the bottom surface. This is advantageous as it is easier to visualise or image a cell or cells that are located in the middle of a bottom surface of a well as compared to at an edge of the bottom surface. Multi-well plates with concave bottom surfaces are commercially available and are sometimes referred to as having U-shaped wells.

The assessment surface is the surface for which presence of the second binding agent at the surface is assessed. The assessment surface need not be delimited by an edge or edges that involve a change in surface shape or configuration (such as the edge between the bottom surface and the cylindrical side surface of a well), and the extent of the assessment surface may be determined simply by the spatial extent of the assessment. By way of example, when the cell culture space is a well of a multi-well plate, the assessment surface may be, for example, part but not all of the bottom surface, or alternatively, the assessment surface may be the entire bottom surface plus an adjacent region of the cylindrical side surface. Of course, alternatively, the assessment surface could simply correspond in extent to the bottom surface of the well.

A cell culture space may have other surfaces. For example, where a cell culture space is a well of a multi-well plate, the assessment surface may be the bottom surface of the well and the vertically extending, cylindrical side surface of the well is then another surface.

The first binding agent is preferably immobilised on the assessment surface before the cells are plated into the associated cell culture space. However, this need not be the case and the assessment surface, having the first binding agent immobilised on it, could be provided by an insert which could be inserted into the growth medium in the cell culture vessel after plating of the cells. However, the immobilised first binding agent needs to be in contact with the growth medium for at least part of, and preferably all of, the incubation so as to allow product of interest secreted by the cells into the growth medium to be localised on the assessment surface.

Hence the steps of the method recited in the claim 1 are not necessarily performed in the order in which they are recited.

The first binding agent may be any agent that is capable of binding to the product of interest, while the first binding agent is immobilised on the assessment surface, so as to localise the product of interest at the assessment surface. Generally speaking, the percentage of the secreted product of interest that becomes localised at the assessment surface, by binding to the first binding agent, should be as high as possible. Preferably, the first binding agent binds the product of interest with sufficient selectively so that binding between the first binding agent and other components of the growth medium does not interfere significantly with localisation of the product of interest at the assessment surface. The first binding agent may bind specifically to the product of interest. For example, the first binding agent may comprise an antibody or antibody fragment capable of binding to the product of interest. Alternatively, if the product of interest is itself an antibody or an antibody fragment, the first binding agent may comprise an epitope to which the product of interest binds.

The first binding agent may be immobilised on the assessment surface in any suitable manner. Many methods of immobilisation are known and described in biochemistry or immunology text books. Generally, the first binding agent will be immobilised on the assessment surface by being coated on the surface. There are commercially available kits suitable for forming coatings and many methods for forming coatings are described in biochemistry or immunology text books.

Preferably, the first binding agent should be immobilised so as to cover the whole of the assessment surface and without covering any other surface of the cell culture space. However, this is not essential and the method may still be performed satisfactorily if only part of the assessment surface is covered with immobilised first binding agent or, alternatively, if other surfaces of the cell culture space are provided with immobilised first binding agent in addition to the assessment surface. By way of example, where the cell culture space is a well of a multi-well plate and the assessment surface is the bottom surface of the well, the invention may still be performed satisfactorily if, in addition to the immobilised first binding agent covering the bottom surface of the well, the first binding agent also covers a lower part of the side, cylindrical surface of the well. In this case, product of interest may bind both to the bottom surface and also to the side cylindrical surface, even though the assessment may only be capable of detecting second binding agent at the bottom surface and not on the side cylindrical surface. This is not ideal as the reduction in the overall amount of secreted product of interest localised at the assessment surface may reduce the sensitivity of the assessment. However, the method is still useful in these circumstances. The amount of second binding agent on the bottom surface of the well (assuming it is detectable) will still be indicative of the amount of product of interest secreted into the growth medium.

Generally, the suspension of cells will be a suspension of a heterogeneous mix of cells. At least some of the cells, but not necessary all, will be capable of producing the product of interest when cultured under appropriate conditions. For example, in the production of monospecific antibodies, myeloma cells are fused with spleen cells to form hybridoma cells. The fusion procedure results in a heterogeneous mix of cells with only a relatively small percentage of the heterogeneous mix being hybridoma cells that are capable of secreting the required monospecific antibody. The current method is applicable to heterogeneous cell mixtures resulting from the fusion of myeloma cells with spleen cells. In this case, the method enables selection of a monoclonal cell colony capable of secreting the required monospecific antibody.

Alternatively, the current method is applicable to heterogeneous mixtures of cells resulting from transfection processes. It is often desired to transfect cells with extraneous nucleic acid to generate a cell line capable of secreting a desired product. The transfection process results in a heterogeneous mix of cells with only a relatively small percentage of the heterogeneous mix being capable of secreting the required product. In this case, the current method enables selection of a monoclonal cell colony capable of secreting the required product.

As used herein, the phrase "single viable cell" means one and only one viable cell but does not exclude the presence or one or more non-viable cells. The term "viable" refers to a cell that is capable of both surviving and replicating under the culture conditions that the cell experiences during the incubation and "non-viable cells" are cells which do not have this capability.

Methods of plating cells to achieve plating of a single viable cell in a cell culture space are known and often referred to as limiting dilution. Such methods involve preparing the suspension of cells to achieve a predetermined concentration of cells in the suspension (i.e. a predetermined number of cells, viable and non-viable, per unit volume of the suspension). The volume of suspension that is to be plated into each cell culture space is known. The required concentration of the cells in the suspension is calculated so that, taking into account the volume of suspension that is to be plated (i.e. dispensed) into each cell culture space, the statistical likelihood is that each cell culture space will receive either a single viable cell or no viable cells at all, but very few cell culture spaces will receive more than one viable cell. The viability of the cells in the suspension may be taken into account in calculating the predetermined concentration so that if a relatively large percentage of the cells are non-viable, then the predetermined concentration of total cells may be increased to take account of the low levels of viability. Where two or more viable cells are plated into a cell culture space two monoclonal colonies or a mixed colony may arise in the cell culture space and such cell culture spaces will generally be discounted from the selection.

In highly preferred embodiments of the invention, the plating of the suspension of the cells in the plurality of cell culture spaces will be done so as to ensure that at least some of the cell culture spaces are plated with one cell and one cell only—regardless of whether the one cell is viable or non-viable. This can be achieved by choosing an appropriate concentration of cells (viable and non-viable) in the suspension, bearing in mind the volume of suspension that is to be plated in each cell culture space. The purpose of this is to be able to select a monoclonal cell colony that has been produced in a cell culture space that was plated with a single viable cell only and with no non-viable cells. If a cell culture space is plated with, for example, one viable cell and one non-viable cell, it is possible that the viable cell will replicate in the cell culture space to produce a monoclonal cell colony. The non-viable cell will not replicate and may die. Monoclonal cell colonies produced from such cell culture spaces may be useful in some applications. However, in many situations it is desirable to select a monoclonal cell colony that has been produced in a cell culture space plated with one cell and one cell only (i.e. one viable cell and no non-viable cells). This may be required for some applications in order to obtain regulatory approval of a product of interest.

As an alternative to using limiting dilution, cells may be plated so as to plate a single viable cell in a cell culture space using fluorescence activated cell sorting.

The growth medium may be any suitable growth medium. The growth medium may provide the cultured cells with everything necessary to survive and replicate. In addition, if any specific chemical is required to allow cells that are capable of secreting the product of interest, to actually secrete the product of interest, then that chemical will normally be included in the growth medium. Preferably the growth medium will be a liquid growth medium. However other types of growth medium, such as semi-solid growth medium may be used.

The cells may be non-adherent or they may adhere to surfaces of the cell culture spaces.

Where liquid growth medium is used and the cells are adherent, the medium may be replaced or partially replaced during the course of the incubation. However, it is preferred to keep the same growth medium in the cell culture spaces without replacement where possible as this avoids potential loss of secreted product of interest and potential disruption to the cells. It is preferable to perform the assessment while the growth medium remains in the cell culture space. Additionally, it is preferable to perform the determination while the growth medium remains in the cell culture space. Preferably, the cells remain in the cell culture space during the assessment.

The second binding agent binds specifically to the product of interest so that presence of the second binding agent at the assessment surface is indicative of presence of product of interest at the assessment surface (the product of interest being bound to the first binding agent). Preferably, the amount of second binding agent bound at the assessment surface is indicative of the amount of product of interest bound at the surface. The relationship between the amount of the second binding agent and amount of the product of interest could be, for example, a positive linear proportional relationship. In one preferred embodiment, the second binding agent comprises an antibody or antibody fragment which binds specifically to the product of interest. Alternatively, if the product of interest is itself an antibody or an antibody fragment, the second binding agent may comprise an epitope to which the product of interest binds.

The second binding agent may be added to the cell culture spaces in the growth medium or it may be added separately from the growth medium either before or after addition of the growth medium. Preferably, the second binding agent is present in the growth medium during at least part of the incubation of the cells in the growth medium and, more preferably, the second binding agent is present in the growth medium during the entire incubation.

At least initially, the second binding agent is generally in solution (or alternatively possibly in suspension) in the growth medium and is not immobilised. If the product of interest is produced by cells in the cell culture space, the product of interest will bind to both the first and second binding agents to form a complex and in this way the second binding agent will become bound at the assessment surface. The product of interest may bind in any order to the first and second binding agents.

Preferably, the first and second binding agents are chosen so that the binding of either one to the product of interest does not hinder the binding of the other one to the product of interest. For example, if the product of interest is an IgG antibody, one of the first and second binding agents may comprise an antibody that binds specifically to the Fc region of the product of interest and the other one of the binding agents may comprise an epitope for the product of interest. Alternatively, the first and second binding agents may each comprise antibodies that bind to respective different epitopes on the product of interest, the epitopes being spaced from one another by a sufficient distance to avoid steric hindrance. Many other arrangements are possible.

As indicated above, the method includes assessing the cell culture spaces for presence of the second binding agent at the assessment surfaces of the cell culture spaces. Presence of the second binding agent at one of the assessment surfaces is an indication of production of the product of interest by the cells in the associated cell culture space.

Preferably, presence of the second binding agent at an assessment surface of a cell culture space is assessed by detection of a label that is associated with the second binding agent. The label may be any agent that can be readily detected. Preferred examples are fluorescent labels. In one preferred embodiment, the label is an integral part of the second binding agent. For example, the label may be a fluorescent agent that has been bound or linked to a specific binding agent to form the second binding agent. By way of a more specific example, the second binding agent may include an antibody or an antibody fragment, to provide the required specific binding capability, and a fluorescent label, such as Fluorescein. The fluorescent label may have been bound or linked to the antibody or antibody fragment in any suitable manner, such as by direct covalent bonding or by using a linking agent which binds to both the fluorescent agent and the antibody or antibody fragment. Fluorescently labelled antibodies are commercially available.

In another preferred embodiment, the label is not an integral part of the second binding agent but is capable of binding specifically to the second binding agent. In this case, the label preferably comprises a specific binding part, such as an antibody or antibody fragment, that enables specific binding to the second binding agent, and also a detectable part, such as a fluorescent agent. The binding part and the detectable part may be bound together in any convenient manner such as by direct covalent binding or by a linking agent which binds to both parts. By way of specific example, if the second binding agent is an IgG antibody of a particular animal species, the label may comprise an antibody that binds to IgG of that animal species together with a detectable part such as a fluorescent agent.

Where the label is not an integral part of the second binding agent, the label can be added to the cell culture space at any convenient time prior to the assessment so long as it is added in a manner and sufficiently in advance of the assessment to enable to label to bind to the second binding agent prior to the assessment.

Where a label is used for the assessment, it will be appreciated that (unless unbound label is removed) the total amount of label in a cell culture space will remain the same regardless of the amount of second binding agent and of the amount of the label which become bound at the assessment surface (and possibly other surfaces) of the cell culture space. This applies both when the label is an integral part of the second binding agent and also when the label is separate from but capable of binding specifically to the second binding agent. Thus, if a relatively large amount of product of interest is produced by cells in a cell culture space, this will result in relatively large amounts of second binding agent and label becoming bound at the assessment surface of the cell culture space (and possibly other surfaces). The amount of label remaining free in the growth medium will be relatively low. Conversely, if a relatively small amount of product of interest is produced, the amount of label bound at the assessment surface (and possibly other surfaces) will be relatively low and the amount of label that remains free in the growth medium will be relatively high. However, in both cases (assuming addition of equal amounts of label) the total amount of bound plus unbound label is the same.

In most cases, it is desirable to be able to detect (and more preferably obtain an indication of the quantity of) label bound to the assessment surface of a cell culture space without having to remove unbound label from the cell culture space. Where the growth medium is a liquid growth medium and the cells are adhered to the assessment surface (or to another surface of the cell culture space), removal of growth medium and consequent removal of unbound label in the growth medium may be possible, but this is often undesirable because it risks dislodging the cells, damaging the cells or disrupting cell growth. It also involves additional complexity of the method, and manipulation, both of which are undesirable. Washing of cell culture spaces to remove unbound label should be avoided wherever possible for the same reasons. Hence, where the assessment is performed by detecting a label that is associated with the second binding agent, the assessment preferably comprises a method of detecting the label, the method being sensitive to label bound to the assessment surface, but less sensitive, or completely insensitive, to label that remains free in the growth medium.

In an especially preferred embodiment of the invention, for each of the cell culture spaces that is assessed for presence of the second binding agent at the assessment surface, the assessment uses an optical focussing device and a light detection device. The optical focussing device focusses light from the assessment surface of the cell culture space onto the light detection device for detection of the light by the light detection device. The focussed light is indicative of the amount of second binding agent present at the assessment surface of the cell culture space. The optical focussing device may be a lens or an array of optical elements (lenses or other optical elements). The light may be visible light, ultraviolet light, or infrared light. The light may be laser light. The detection device may be any device capable of detecting the light and may comprise, for example, a CCD detector, a CMOS detector or an sCMOS detector. Alternatively, the detection device may comprise a photomultiplier tube (PMT). Preferably, the light detection device produces, for each cell culture space that is assessed, a respective signal indicative of the intensity of light received from the assessment surface. The intensity is preferably indicative of the amount of second binding agent at the assessment surface. The light is preferably emitted by a label, which, as discussed above, may be an integral part of the second binding agent or which may be separate from and capable of specifically binding to the second binding agent. In especially preferred embodiments, the label is a fluorescent label. In this case the assessment includes illuminating the cell culture space with excitation light capable of exciting the fluorescent label. Fluorescent light emitted by the fluorescent label is detected by the light detection device. The intensity of the emitted fluorescent light gives an indication of the amount of label, and indirectly of the amount of second binding agent and the amount of product of interest at the assessment surface.

Even more preferably, the optical properties of the optical focusing device are such so that light from elsewhere in the cell culture space, at locations spaced from the assessment surface, is not brought into focus by the optical focussing device at the light detection device (although it may pass through the optical focussing device). In this way, the light detection device is less sensitive to, or does not detect at all, light emitted from elsewhere in the cell culture space, such as light emitted by unbound label in the growth medium.

Preferably, the assessment gives a quantitative indication of the amount of second binding agent, and of the product of interest, present at the assessment surface.

It is not necessary to assess all of the cell culture spaces for presence of the second binding agent at the assessment surface. For example, if it is determined that a cell culture space contains more than one cell colony, that cell culture space may be discounted and need not be assessed.

As indicated above, the method includes determining, for at least some of the cell culture spaces, whether the cell culture space contains a single cell colony that is derived from a single cell. The term "single cell colony" is used to mean one and only one cell colony. It will be appreciated that a single cell colony derived from a single cell may be produced in a cell culture space that is plated with a single viable cell and with one or more non-viable cells or, alternatively, in a cell culture space that is plated with a single viable cell only and with no non-viable cells. In order to distinguish between these two possibilities, the determination preferably comprises determining whether the cell culture space was plated with one cell and one cell only (i.e. a viable cell).

The determination is preferably performed by microscopic visualisation of cells in the cell culture space at a plurality of time points during the incubation. For example, where liquid growth medium is used, the cells may be visualised as soon as the cells have settled on the bottom surface of the cell culture space after plating (typically at about an hour after plating). In addition, the cells may be visualised, for example, at 1, 2, 4 and 8 days after plating. The visualisation is preferably performed by an automated apparatus using an appropriate camera and image processing means. Suitable apparatus is commercially available. By analysing a series of images of a cell culture space over the course of the incubation, it is possible to determine whether a cell colony produced in the cell culture space was derived from a single cell, and also whether the cell culture space was plated with one cell and one cell only. The visualisation may be performed using transmitted light microscopy, such as brightfield, phase contrast and Nomarsky.

Preferably, the determination is performed by an automated apparatus which obtains and stores a respective series of images for each cell culture space. Each series of images comprises images at different time points during the incubation. The apparatus preferably does not analyse the images until the assessment has been made for the second binding agent at the assessment surface, as discussed above. It is then possible to analyse only those series of images that belong to cell culture spaces which show a relatively high level of second binding agent at the assessment surface. A high level of second binding agent at an assessment surface is indicative that the associated cell culture space contains cells which produce high levels of the product of interest. Often, it is only these "high producer" cells which are of interest. In a preferred example, the method includes defining a threshold for the assessment of the second binding agent and only analysing those series of images for which the associated cell culture space exceeds the threshold.

The method includes selecting a cell culture space using the assessment and the determination. The selected cell culture space will contain a single monoclonal cell colony which secretes the product of interest. Hence generally, the selected cell culture space will have demonstrated a relatively high level of second binding agent at the assessment surface during the assessment indicating high levels of production of the product of interest. The determination will have revealed that the cell culture space contains a single cell colony derived from a single cell. Preferably, the cell culture space will have been plated with one cell and one cell alone.

Preferably, the method comprises, for at least some of the cell culture spaces, obtaining an indication of a rate of growth of the cells in the cell culture space. The indication is used in the selection of the cell culture space. The selected cell culture space may have a rate of cell growth above a predetermined threshold. Alternatively, the selected cell culture space may have a rate of cell growth that is relatively high compared to the growth rates of cells in other cell culture spaces. The indication of the rate of cell growth may be obtained by visualising the cells in a cell culture space at a plurality of time points during the incubation. The indication may comprise comparing estimates of percentage cell confluence at different time points during the application.

In accordance with a second aspect of the invention, there is provided automated apparatus for performing a method according to the first aspect of the invention, the apparatus comprising: an optical focussing device; a light detection device; a holder for holding a multi-well plate; a translation mechanism for relative movement between the holder and the optical focussing device and the light detection device; and a controller configured for performing the method of the first aspect of the invention.

The following is a more detailed description of embodiments of the invention, by way of example, reference being made to the appended schematic drawings in which.

COMPLEXES AT THE ASSESSMENT SURFACE

Figure 1:
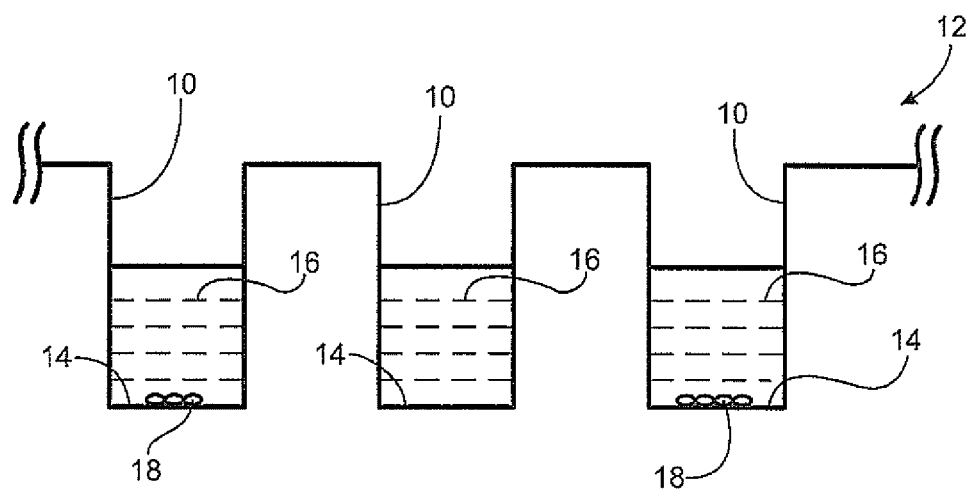
FIG. 1 is a cross-sectional representation of part of a multi-well culture plate showing three wells each having a respective assessment surface.

FIG. 1 shows three wells 10 of a multi-well plate 12. Each well 10 has a respective bottom surface 14 which for the purposes of the current method serves as an assessment surface 14. As shown in FIG. 1, each well contains growth medium 16. Two of the wells are shown with cell colonies 18.

Figure 2:
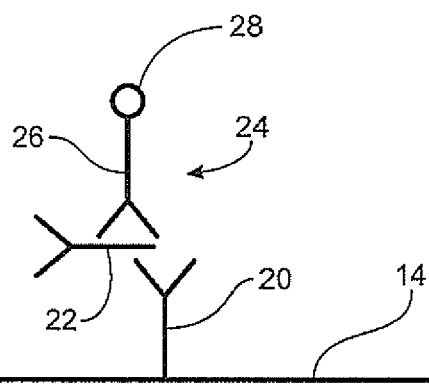
FIG. 2 shows an assessment surface, a first binding agent, a product of interest and a second binding agent, all of a first embodiment of the current method.
Figure 3:
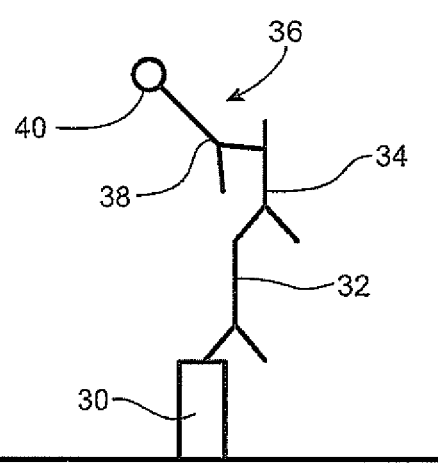
FIG. 3 shows an assessment surface, a first binding agent, a product of interest, a second binding agent, and a separate label, all of a second embodiment of the current method.
Figure 4:
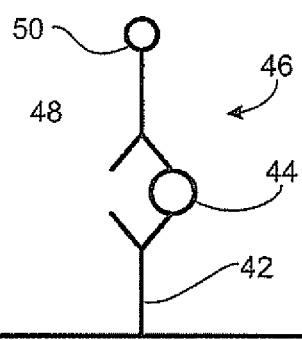
FIG. 4 shows an assessment surface, a first binding agent, a product of interest, and a second binding agent, all of a third embodiment of the current method.

FIGS. 2 to 4 show various examples of different types of complexes that form at an assessment surface 14. The assessment surface 14 may be, for example, any one of the bottom surfaces 14 shown in FIG. 1.

In the first embodiment shown in FIG. 2, the assessment surface 14 is coated with a first binding agent 20 which is an anti-IgG antibody 20. For simplicity of representation, only one molecule of the first binding agent 20 is shown although it will be appreciated that many molecules of the first binding agent 20 will be bound to and will cover the assessment surface 14. The product of interest 22 in this embodiment is an IgG antibody 22 and the first binding agent 20 binds specifically to the Fc region of the product of interest 22. The second binding agent 24 comprises an anti-IgG antibody 26 covalently linked to a fluorescent label 28. The anti-IgG antibody 26 of the second binding agent 24 also binds specifically to the Fc region of the product of interest 22. The first binding agent 20 and the second binding agent 24 bind to different and spaced epitopes on the product of interest 22.

It will be appreciated that, in all embodiments, there should be no direct binding of the second binding agent to the first binding agent. Hence, in the first embodiment shown in FIG. 2, the first binding agent 20 and the anti-IgG antibody 26 of the second binding agent 24 are chosen so that they do not bind to one another. For example, if the product of interest 22 is a mouse IgG, the first binding agent 20 and the anti-IgG antibody 26 of the second binding agent 24 may be anti-mouse IgG antibodies from a different animal species.

In the second embodiment shown in FIG. 3, the assessment surface 14 is coated with a first binding agent 30 which is a protein 30 having an epitope. For simplicity of representation, only one molecule of the first binding agent 30 is shown although it will be appreciated that many molecules of the first binding agent 30 will be bound to and will cover the assessment surface 14. The product of interest 32 in this embodiment is an IgG antibody 32 and the epitope of the first binding agent 30 binds specifically to the product of interest 32. The second binding agent 34 is an anti-IgG antibody 34. The second binding agent 34 binds specifically to the Fc region of the product of interest 32. In this embodiment, the label 36 is separate from and not an integral part of the second binding agent 34. The label 36 comprises an anti-IgG antibody 38 covalently linked to a fluorescent molecule 40. The anti-IgG antibody 38 of the label 36 binds specifically to the Fc region of the second binding agent 34.

In the third embodiment shown in FIG. 4, the assessment surface 14 is coated with a first binding agent 42 which is an antibody 42. For simplicity of representation, only one molecule of the first binding agent 42 is shown although it will be appreciated that many molecules of the first binding agent 42 will be bound to and will cover the assessment surface 14. The product of interest 44 in this embodiment is a protein 44 (but not an antibody). The first binding agent 42 binds specifically to the product of interest 44. The second binding agent 46 comprises an antibody 48 covalently linked to a fluorescent molecule 50. The antibody 48 of the second binding agent 46 also binds specifically to the product of interest 44. The first binding agent 42 and the second binding agent 46 bind to different and spaced epitopes on the product of interest 44.

As demonstrated by FIGS. 2 to 4, the precise nature of the complex can be varied. The principle of operation is that the first binding agent 20, 30, 42 localises the product of interest 22, 32, 44 (where present) at the assessment surface 14. Presence of the product of interest 22, 32, 44 at the assessment surface 14 causes binding of the second binding agent 24, 34, 46 and the label 28, 36, 50 at the assessment surface. In this way presence of the label 28, 36, 50 at the assessment surface 14 is indicative of production of the product of interest.

First Specific Example of Method

The following Example demonstrates how the current method may be used to generate and subsequently select a monoclonal cell colony, having a sufficient rate of growth and secreting a relatively high amount of a desired monospecific IgG antibody, starting from a heterogeneous mixture of cells.

The monospecific IgG antibody is to be used in the production of a pharmaceutical product.

The cells used in the current Example are Chinese Hamster Ovary DG44 (CHO-DG44) cells that have been transfected to produce the desired monospecific IgG antibody. The desired monospecific antibody is, in this example, a human antibody. More specifically, the cells have been transfected with two vectors, one coding for the light chain of the desired IgG antibody and the other coding for the heavy chain of the desired IgG antibody. One (or possibly both) of the vectors also codes for the enzyme dihydrofolate reductase (DHFR).

The transfection process results in a heterogeneous mixture of cells. Only a small number of the cells have the desired characteristics of a sufficient growth rate and relatively high secretion of the desired IgG antibody. It is this heterogeneous mixture of cells that is used in the current Example.

Firstly, a 96 well plate is prepared for use in the method. This requires the wells of the plate to be provided with a coating of recombinant anti-human IgG antibody to act as the first binding agent. A coating solution of the anti-human IgG antibody (15 μg/ml) is prepared in filtered, 1× coating buffer. The coating buffer is a commercially available buffer available under Catalogue No. 6245 from ImmunoChemistry Technologies LLC of Bloomington, Minn., USA. In this Example, the wells of the 96 well plate are U-shaped wells with concave bottom surfaces. A 100 μl aliquot of the coating solution is placed in each well of the plate. This is sufficient to cover the concave bottom surfaces and also small lower regions of the cylindrical side surfaces. The coating solution is left in the wells for 2 hours at room temperature. The wells are then washed 3 times with PBS.

It is desirable to use a recombinant anti-human IgG antibody, rather than, for example, a polyclonal anti-human IgG antibody raised in an animal species, to avoid possible contamination by material of animal origin.

After the 96 well plate has been prepared, a suspension of the heterogeneous mixture of cells is prepared in growth medium. The growth medium used in this Example is Gibco CD OptiCHO™ chemically defined medium available from Life Technologies. The mixture of cells is suspended in the growth medium to a dilution of between 0.5 to 1.5 cells/ml.

The CIH-DG44 cell line that is used for the transfection does not express DHFR endogenously. As a result, the cells will not grow and replicate in the CD OptiCHO™ medium unless they express DHFR from the DHFR coding vector (also coding for one of the IgG chains). This acts as a first line of selection. As a second selection method, methotrexate can be used. The methotrexate is an inhibitor of DHFR and is included in the growth medium as it tends to amplify the DHFR gene and also the IgG gene included on the same vector.

In addition, a conjugate consisting of a recombinant anti-human IgG antibody linked to a fluorescent label is added to the cell suspension as the second binding agent. The anti-human IgG antibody of the second binding agent is the same antibody used for the first binding agent, but in this case linked to a suitable fluorescent label such as fluorescein. A suitable conjugate is Recombinant CloneDetect™ human IgG(Fc) specific available from Molecular Devices, LLC of Sunnyvale, Calif., USA. The conjugate is added to the cell suspension to a final concentration of 1 μg/ml and the suspension is mixed gently.

Because the same recombinant anti-human IgG antibody is used both for the first binding agent and also for the specific binding part of the second binding agent, there is no direct binding between the first and second binding agents.

The cells are then plated in the wells of the 96 well plate by pipetting a 200 μl aliquot of the cell suspension, with the second binding agent, into each well. If the concentration of cells is 1.0 cells/ml, then this will give an average of 0.2 cells per well. Hence, many of the wells will have no cells at all. A significant number will have one cell only and only a few wells (if any) will have two cells or more.

After plating the 96 well plate is incubated at 37° C. with 5% CO2.

After about an hour, the cells will have settled to the bottom of the wells and, at this time, each well is imaged using an ImageXpress® Micro high speed imaging microscope available from Molecular Devices, LLC of Sunnyvale, Calif., USA. For each well, the microscope captures a first image using transmitted white light and a second fluorescent image. For the fluorescent image, an excitation light of 470 nm is used and emission light of 535 nm is detected. The images are stored for analysis.

The 96 well plate is incubated at 37° C. with 5% CO2 for 8 days and each well is imaged, as for the initial 1 hour timepoint described above, at 1, 2, 4 and 8 days.

During the 8 day incubation, cell colonies form, by cell replication, in those wells which are plated with one or more viable cells. In any well in which only a single viable cell is plated, any colony which forms in that well is a monoclonal cell colony.

Some colonies secrete the desired monospecific IgG antibody. The secreted monospecific antibody binds both to the second binding agent (i.e. the anti-human IgG antibody-fluorescein conjugate) and to the immobilised first binding agent. Hence, in each well in which the desired monospecific IgG antibody is secreted, a complex comprising first binding agent, secreted IgG antibody and second binding agent forms at the surface regions of the well that are coated with the first binding agent.

Figure 5:
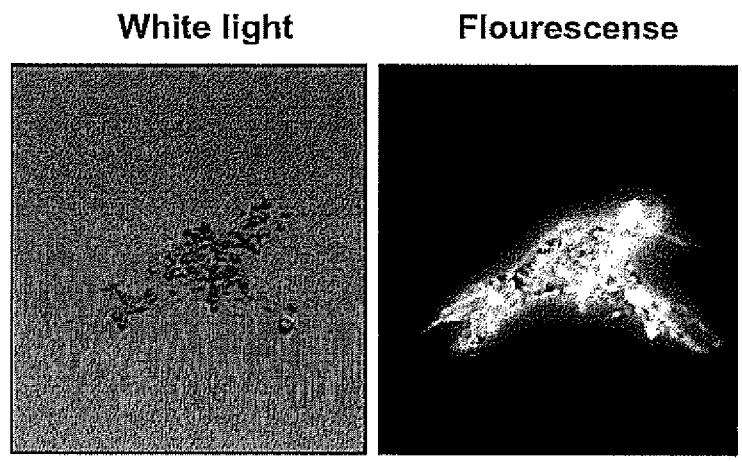
FIG. 5 shows a white light image and a fluorescent image of a cluster of cells which secretes a relatively large amount of a desired monospecific IgG antibody.

The purpose of the fluorescent images is to detect and quantify the fluorescent label (and hence the complex). The intensity of fluorescence is indicative of the amount of fluorescent label bound in the complex as described above. A fluorescent image together with a white light image for a highly productive cluster of cells is shown in FIG. 5.

The optics of the ImageXpres® Micro microscope are preferably set so that the fluorescent images, for each well, cover at least the bottom concave surface of the well. The images may also cover those regions of the side cylindrical walls that are coated with first binding agent, although this is not necessary. The extent of coverage of the fluorescent images determines the extent of the assessment surface.

Towards the end of the incubation, any wells in which cell colonies have developed which are capable of secreting significant amounts of the desired IgG antibody can be detected by analysing the fluorescent images for fluorescence at the assessment surfaces. This analysis also allows the wells to be ranked in relation to the amount of secreted desired IgG antibody.

Figure 6:
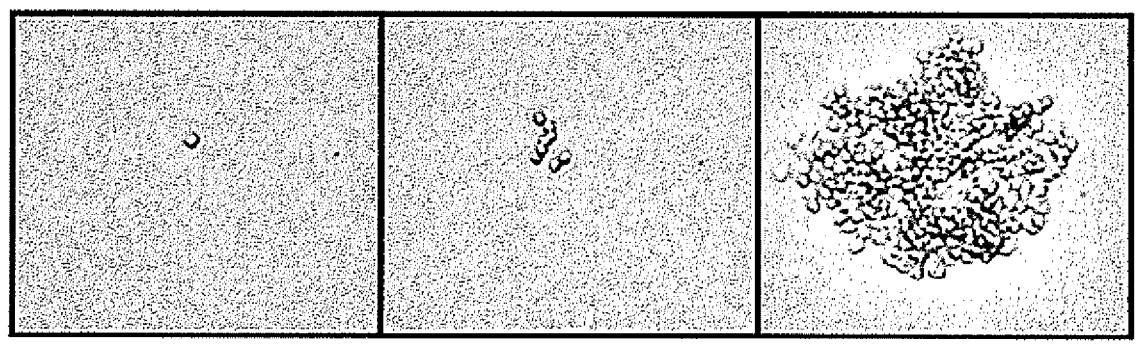
FIG. 6 is a sequence of white light images showing the development of a monoclonal cell colony from a single cell.

Those wells which have the highest levels of fluorescence, indicative of relatively high levels of secreted IgG antibody, are then assessed to see whether the wells contain a single cell colony derived from a single cell. This is done by analysing the white light images for each well in question. By viewing the images backwards in time order, from the day 8 image to the 1 hour image, and assessing the number of cells in each image, it is possible to determine whether a well has a single colony derived from a single cell (i.e. a monoclonal cell colony). FIG. 6 shows a sequence of white light images of a single well showing the development of a cell colony (see the right hand image taken at the end of the incubation) from a single cell (see the left hand image taken at 1 hour after plating).

Finally one or more wells are selected. Each selected well is selected on the basis of having a relatively high secretion of the desired IgG antibody from a single monoclonal cell colony. Preferably, each selected well had only one cell plated in it (rather than one viable cell plus one or more non-viable cells). The rate of cell growth may also be assessed by assessing the number of cells in the images taken at the different time points in the incubation, and the selection may include selecting a well which exhibits a satisfactory rate of cell growth.

After the 8 day incubation, selected monoclonal colonies may be re-plated to larger wells. Production of the desired IgG antibody, and growth rates may be monitored using the same methods described above to confirm clone stability.

Protein G could be used instead of the recombinant anti-human IgG antibody. In this case, protein G would be coated on the assessment surface as the first binding agent. For the second binding agent, protein G would be conjugated with the fluorescent label.

Second Specific Example of Method

The following Example demonstrates how the current method may be used to generate and subsequently select a monoclonal cell colony, having a sufficient rate of growth and secreting a monospecific IgG antibody with specificity to a protein of interest, starting from a heterogeneous mixture of cells.

The cells used in the current Example are hybridoma cells generated by fusion of myeloma cells and mouse spleen cells. The fusion process gives a heterogeneous mixture of cells only a relatively small proportion of which produce antibody with the desired specificity to the protein of interest.

Firstly, a 96 well plate is prepared for use in the method. This requires the wells of the plate to be provided with a coating of a protein (antigen) to which the desired antibody binds. A coating solution of the protein (15 µg/ml) is prepared in filtered, 1× coating buffer. The coating buffer is a commercially available buffer available under Catalogue No. 6245 from ImmunoChemistry Technologies LLC of Bloomington, Minn., USA. In this Example, the wells of the 96 well plate are U-shaped wells with concave bottom surfaces. A 100 µl aliquot of the coating solution is placed in each well of the plate. This is sufficient to cover the concave bottom surfaces and also small lower regions of the cylindrical side surfaces. The coating solution is left in the wells for 2 hours at room temperature. The wells are then washed 3 times with PBS.

After the 96 well plate has been prepared, a suspension of the heterogeneous mixture of cells is prepared in growth medium. The growth medium used in this Example is IMDM with 20% foetal bovine serum. The mixture of cells is suspended in the growth medium to a dilution of between 0.5 to 1.5 cells/ml.

In addition, a conjugate consisting of an anti-IgG antibody linked to a fluorescent label is added to the cell suspension as the second binding agent. The antibody of the conjugate is specific to mouse IgG. A suitable conjugate is CloneDetect mouse IgG specific available from Molecular Devices LLC of Sunnyvale, Calif., USA. The conjugate is added to the cell suspension to a final concentration of 1 µg/ml and the suspension is mixed gently.

The cells are then plated in the wells of the 96 well plate by pipetting a 200 µl aliquot of the cell suspension, with the second binding agent, into each well. If the concentration of cells is 1.0 cells/ml, then this will give an average of 0.2 cells per well. Hence, many of the wells will have no cells at all. A significant number will have one cell only and only a few wells (if any) will have two cells or more.

After plating the 96 well plate is incubated at 37° C. with 5% CO2.

After about an hour, the cells will have settled to the bottom of the wells and, at this time, each well is imaged using an ImageXpres® Micro high speed imaging microscope available from Molecular Devices, LLC of Sunnyvale, Calif., USA. For each well, the microscope captures a first image using transmitted white light and a second fluorescent image. For the fluorescent image, an excitation light of 470 nm is used and emission light of 535 nm is detected. The images are stored for analysis.

The 96 well plate is incubated at 37° C. with 5% CO2 for 8 days and each well is imaged, as for the initial 1 hour timepoint described above, at 1, 2, 4 and 8 days.

During the 8 day incubation, cell colonies form, by cell replication, in those wells which are plated with one or more viable cells. In any well in which only a single viable cell is plated, any colony which forms in that well is a monoclonal cell colony.

Some colonies secrete the desired monospecific IgG antibody. The secreted antibody binds both to the anti-IgG antibody part of the second binding agent and also to the immobilised protein antigen. Hence, in each well in which the desired IgG antibody is secreted, a complex comprising the protein antigen, secreted IgG antibody and the second binding agent forms at the coated surface regions of the well.

As for the first Example, the purpose of the fluorescent images is to detect and quantify the fluorescent label (and hence the complex). The optics of the ImageXpres® Micro microscope are preferably set so that the fluorescent images, for each well, cover the bottom concave surface of the well. The extent of coverage of the fluorescent images determines the extent of the assessment surface.

Towards the end of the incubation, any wells in which cell colonies have developed which secrete antibody with the desired specificity can be detected by analysing the fluorescent images for fluorescence at the assessment surfaces. This analysis also allows the wells to be ranked in relation to the amount of secreted desired IgG antibody.

Those wells which have fluorescent signal, indicative of the presence of IgG antibody with the desired specificity, are then assessed to see whether the wells contain a single cell colony derived from a single cell. This is done as for the First Example by analysing the white light images for each well in question.

Finally one or more wells are selected. Each selected well is selected on the basis of secreting antigen-specific IgG antibody from a single monoclonal cell colony. Preferably, each selected well had only one cell plated in it (rather than one viable cell plus one or more non-viable cells). The rate of cell growth may also be assessed by assessing the number of cells in the images taken at the different time points in the incubation, and the selection may include selecting a well which exhibits a satisfactory rate of cell growth.

Apparatus Suitable to Perform Method

Figure 7:
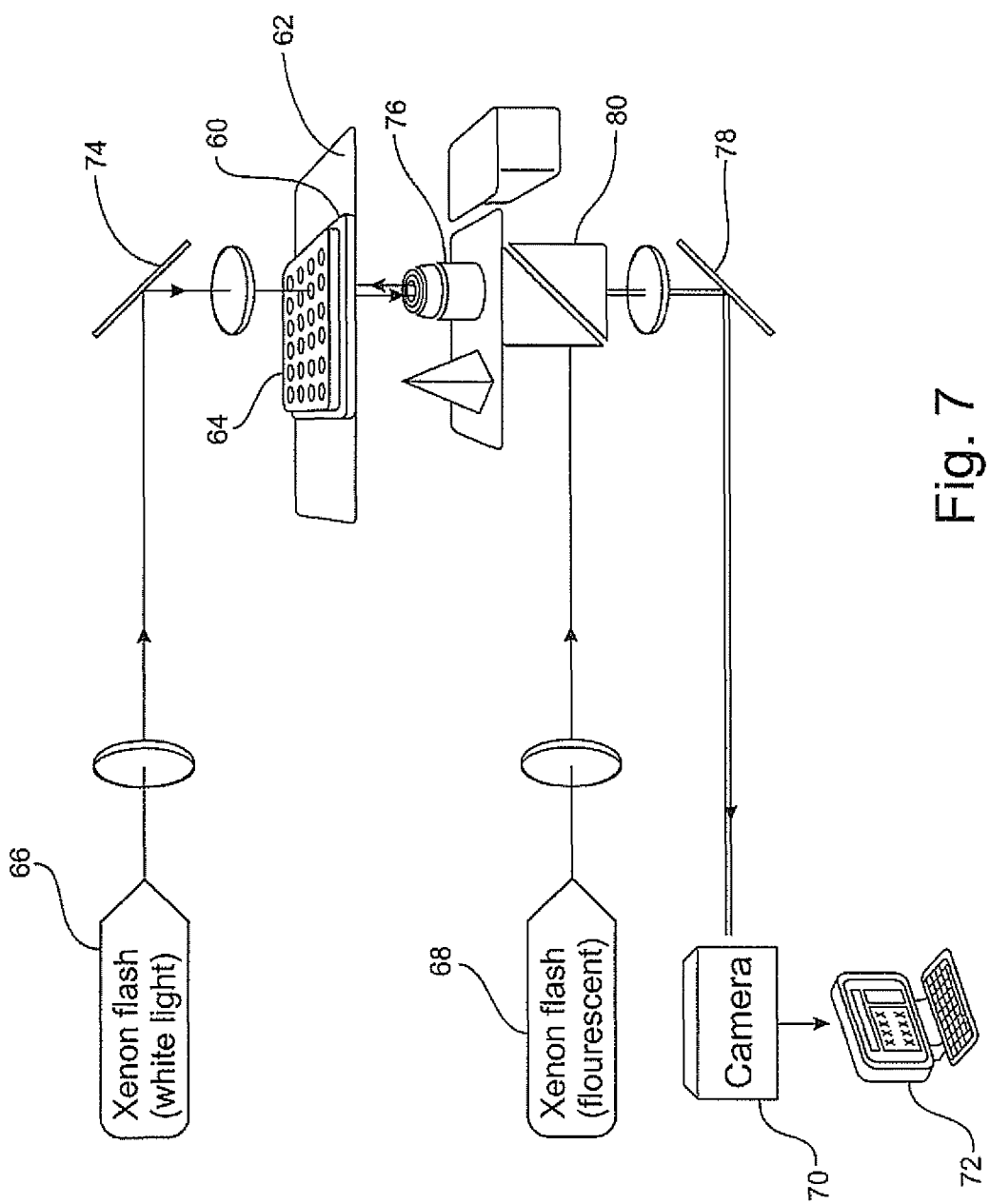
FIG. 7 is a diagrammatic representation of apparatus suitable for performing the current method.

FIG. 7 shows apparatus suitable for performing the current invention.

The apparatus comprises a plate holder 60 which is shown holding a multi-well plate 64. The plate holder 60 is mounted on an XY stage 62 which moves the plate holder 60 in the X and Y directions; that is to say in orthogonal directions in a horizontal plane. In this way, any well of the multi-well plate 64 can be selected and imaged by the apparatus.

The apparatus also comprises a first white light source 66 for white light imaging, a second light source 68 for fluorescent imaging, and a camera 70. The camera 70 detects light and produces images during both white light and fluorescent imaging.

The camera passes images to a computer 72 which both stores and analyses images. The computer 72 also controls the operation of the apparatus.

During white light imaging, light is emitted by the first light source 66 and, after reflection by a first mirror 74, passes though the selected well of the multi-well plate 64. The light is focussed by a 10× lens array 76 onto a second mirror 78 which reflects the light onto the camera 70 for generation of an image of the bottom surface of the selected well including any cells that are present on the bottom surface.

During fluorescence imaging, light is emitted by the second light source 68 (which includes a filter so that the emitted light has the appropriate excitation wavelength) to an optical block 80. The optical block 80 directs the light through the lens array 76 which focusses light onto the bottom surface of the selected well of the multi-well plate 64. The excitation light excites any fluorescent label located at the bottom surface of the selected well. Fluorescent light emitted by fluorescent label passes back through the lens array 76 and through the optical block 80 to the second mirror 78 which reflects the light to the camera 70 for generation of an image. The emitted fluorescent light is also subject to suitable filtration by a filter which is not shown.

During fluorescent imaging, the lens array 76 serves to focus both the excitation and emission light so that the apparatus detects substantially only light from fluorescent label that is located at the bottom surface of the selected well. Although unbound label will be present in the growth medium in the well, the apparatus is largely insensitive to unbound label.

The invention claimed is:

1. A method of selecting a monoclonal cell colony that secretes a product of interest, comprising:
   providing a plurality of cell culture spaces, each cell culture space having a respective assessment surface;
   providing each said assessment surface with a first binding agent that is immobilised on the assessment surface;
   plating a suspension of cells in the plurality of cell culture spaces so that at least some of the cell culture spaces are plated with a single viable cell;
   incubating the cells in a growth medium in the cell culture spaces to cause replication of the cells, wherein at least some of the cells secrete a product of interest;
   providing a second binding agent in the cell culture spaces, the second binding agent not being immobilised;
   wherein each of the first and second binding agents binds to the product of interest so that secretion of the product of interest by cells in any one of the cell culture spaces leads to a complex comprising the first binding agent, the product of interest and the second binding agent forming at the corresponding assessment surface of the said one cell culture space;
   assessing each of at least some of the cell culture spaces for presence of the second binding agent at the assessment surface of the cell culture space;
   determining for each of at least some of the cell culture spaces whether the cell culture space contains a single cell colony that is derived from a single cell; and
   selecting a cell culture space using said assessment and said determination, the selected cell culture space containing a single monoclonal cell colony which secretes the product of interest.

2. A method according to claim 1, wherein for each of said at least some cell culture spaces that are assessed, said assessment for presence of the second binding agent uses an optical focussing device and a light detection device, the optical focussing device focussing light from the assessment surface of the cell culture space onto the light detection device for detection of the light by the light detection device, the focussed light being indicative of an amount of second binding agent present at said surface of the cell culture space.

3. A method according to claim 2, wherein light from locations in the cell culture space spaced from the assessment surface, is not brought into focus by the optical focussing device at the light detection device.

4. A method according to claim 2 or claim 3, wherein a light emitting label is associated with the second binding agent, said light emitting label emitting said light focussed by the optical focussing device.

5. A method according to claim 1, wherein a light emitting label is associated with the second binding agent and said assessment of the assessment surface for the presence of the second binding agent comprises detecting light emitted by the label bound at the assessment surface, wherein a portion of the label is not bound at the assessment surface and is located in the cell culture space away from the assessment surface, and wherein the assessment is less sensitive, or completely insensitive, to light emitted by the portion of the label.

6. A method according to claim 4, wherein the light emitting label emits fluorescent light and the method includes exciting the light emitting label with excitation light.

7. A method according to claim 1 or claim 2, wherein for each of said at least some cell culture spaces for which said determination is performed, said determination comprises determining whether the cell culture space was plated with one cell and one cell only, and wherein said selected cell culture space was plated with one cell and one cell only.

8. A method according to claim 1 or claim 2, wherein for each of said at least some cell culture spaces for which said determination is performed, said determination comprises microscopic visualisation of cells in the cell culture space at a plurality of time points during said incubation.

9. A method according to claim 1 or claim 2, wherein said cell culture spaces are, respectively, wells of a multi-well culture plate, is a 96 well plate or a 384 well plate.

10. A method according to claim 1, including identifying a subset of the cell culture spaces on the basis of said assessment of the surfaces for presence of the second binding agent, the cell culture spaces of the subset having greater levels of the second binding agent present at the assessment surfaces than those cell culture spaces that are not part of the subset, and wherein said determination of whether the cell culture space contains a single cell colony that is derived from a single cell is only carried out on the cell culture spaces of the subset.

11. A method according to claim 10, including, for each cell culture space, obtaining a respective series of images over time and storing the series of images, and wherein said determination of whether the cell culture space contains a single cell colony that is derived from a single cell comprises analysing the series of images from each cell culture space of the subset.

12. A method according to claim 1, comprising, for each of at least some of the cell culture spaces, obtaining an indication of a rate of growth of cells in the cell culture space, the indication being used in said selection of said cell culture space.

* * * * *